US012567172B2

(12) United States Patent
Rao et al.

(10) Patent No.: US 12,567,172 B2
(45) Date of Patent: Mar. 3, 2026

(54) SYSTEM AND METHOD FOR OBTAINING ACCURATE MEASUREMENTS AND QUANTIFICATION OF X-RAY IMAGE FROM ESTIMATION OF KEY ANATOMICAL LOCATIONS

(71) Applicant: GE Precision Healthcare LLC, Wauwatosa, WI (US)

(72) Inventors: Gireesha Chinthamani Rao, Pewaukee, WI (US); Ravi Soni, San Ramon, CA (US); Gopal B. Avinash, Concord, CA (US); Poonam Dalal, Brookfield, WI (US); Chen Liu, Mountain View, CA (US); Molin Zhang, Cambridge, MA (US); Zita Herczeg, Szeged (HU)

(73) Assignee: GE Precision Healthcare LLC, Wauwatosa, WI (US)

( * ) Notice: Subject to any disclaimer, the term of this patent is extended or adjusted under 35 U.S.C. 154(b) by 238 days.

(21) Appl. No.: 17/975,889

(22) Filed: Oct. 28, 2022

(65) Prior Publication Data

US 2023/0169682 A1 Jun. 1, 2023

Related U.S. Application Data

(60) Provisional application No. 63/283,350, filed on Nov. 26, 2021.

(51) Int. Cl.
*G16H 30/40* (2018.01)
*A61B 6/00* (2006.01)
(Continued)

(52) U.S. Cl.
CPC .............. *G06T 7/74* (2017.01); *A61B 6/5217* (2013.01); *A61B 6/5229* (2013.01); *G06T 7/337* (2017.01);
(Continued)

(58) Field of Classification Search
CPC . G06T 7/74; G06T 7/337; G06T 2207/10116; G06T 2207/20021;
(Continued)

(56) References Cited

U.S. PATENT DOCUMENTS

2014/0323845 A1 10/2014 Forsberg
2015/0272695 A1 10/2015 Kubiak
(Continued)

OTHER PUBLICATIONS

IB Lab LAMA CE Leg Angle Measurement Assistant, https://www.imagebiopsy.com/product/lama-ce.
(Continued)

Primary Examiner — David J Makiya
Assistant Examiner — Mamadou Faye
(74) Attorney, Agent, or Firm — Boyle Fredrickson, S.C.

(57) ABSTRACT

An artificial intelligence (AI) measurement system for an X-ray image is employed either as a component of the X-ray imaging system or separately from the X-ray imaging system to automatically scan post-exposure X-ray images to detect and locate various landmarks of the anatomy presented within the X-ray image. A set of key image features approximating the locations of the landmarks having known distance relationships to one another is overlaid onto the X-ray image. The positions of the key image features are then adjusted to correspond to the landmarks within the X-ray image. These adjustments are made relative to the prior known distance relationships between the key features, which enables the measurement system to readily calculate desired angular and length measurements between landmarks as a result.

16 Claims, 8 Drawing Sheets

(51) Int. Cl.
    *G06T 7/33*            (2017.01)
    *G06T 7/73*            (2017.01)

(52) U.S. Cl.
    CPC .... *G16H 30/40* (2018.01); *G06T 2207/10116*
        (2013.01); *G06T 2207/20021* (2013.01); *G06T*
        *2207/20081* (2013.01); *G06T 2207/30168*
                         (2013.01)

(58) Field of Classification Search
    CPC . G06T 2207/20081; G06T 2207/30168; G06T
        2207/20084; G06T 2207/30008; G06T
        7/60; G06T 7/0012; G06T 7/11; G06T
        17/20; G06T 2207/10081; A61B 6/5217;
        A61B 6/5229; A61B 6/461; A61B 6/466;
        A61B 6/52; A61B 6/00; A61B 6/40;
        A61B 6/4021; A61B 6/4429; A61B
        6/505; A61B 6/5205; A61B 6/5223;
                        G16H 30/40
    See application file for complete search history.

(56)                   References Cited

U.S. PATENT DOCUMENTS

| | | | |
|---|---|---|---|
| 2016/0331463 A1* | 11/2016 | Nötzli | A61B 34/10 |
| 2021/0137634 A1* | 5/2021 | Lang | A61B 34/20 |
| 2021/0391058 A1* | 12/2021 | Kostrzewski | G16H 20/40 |

OTHER PUBLICATIONS

Lower Limb Length Discrepancy, Ortho Info, https://orthoinfo.aaos.org/en/diseases--conditions/limb-length-discrepancy/.
Patrick Langechuan Liu, Self-supervised Keypoint Learning—A Review, Towards Data Science, May 16, 2020, https://towardsdatascience.com/self-supervised-keypoint-learning-aade18081fc3.
EP application 22207479.1 filed Nov. 15, 2022—extended Search Report issued Apr. 13, 2023, 7 pages.

* cited by examiner

SYSTEM AND METHOD FOR OBTAINING ACCURATE MEASUREMENTS AND QUANTIFICATION OF X-RAY IMAGE FROM ESTIMATION OF KEY ANATOMICAL LOCATIONS

CROSS-REFERENCE TO RELATED APPLICATIONS

The present application claims priority from U.S. Provisional Patent Application Ser. No. 63/283,350, filed on Nov. 26, 2021, the entirety of which is expressly incorporated herein by reference for all purposes.

FIELD OF THE DISCLOSURE

The present disclosure relates to X-ray imaging systems, and more particularly to X-ray imaging systems including ancillary image processing systems to improve workflow and the quality of images produced by the X-ray systems.

BACKGROUND OF THE DISCLOSURE

A number of X-ray imaging systems of various designs are known and are presently in use. Such systems are generally based upon generation of X-rays that are directed from an X-ray source toward a subject of interest. The X-rays traverse the subject and impinge on a detector, for example, a film, an imaging plate, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments.

With regard to the X-ray images produced by the X-ray systems, it is desirable for a radiologist or other medical practitioner to obtain various angular and length measurements of the anatomical components illustrated in the X-ray image for diagnosis and other purposes. In order to obtain these measurements, it is necessary for the radiologist to be able to calculate the distances between different points and/or areas of the anatomy presented in the X-ray image. This process is normally accomplished utilizing a measurement algorithm formed as a part of or separate from the X-ray system that can provide these measurements.

In calculating the desired measurements, as shown in FIG. 1 a prior art AI model/algorithm 100 reviews the anatomy present within the X-ray image 102 input to the model 100 and performs an anatomy landmark segmentation on the anatomy. The anatomy landmark segmentation 105 identifies a number of particular and important areas, points or structures 104 of the anatomy in the X-ray image 102 that function as specified landmarks known by the measurement algorithm Once identified within the X-ray image 102, the areas 104 are run through a complex geometric/trigonometry post-processing algorithm/computation 106 that provides the desired measurements 112 between the areas 104 shown in the X-ray image 102.

As shown in FIGS. 1-2, prior art methods and systems for providing measurements of this type from X-ray images 102 include systems 108 incorporating a single AI model 100 (FIG. 1) that performs a multiple landmark segmentations on the X-image 102, and alternative systems 110 that incorporate multiple AI models 100 (FIG. 2), each AI model 100 configured to provide an anatomy segmentation 105 of a single area 104 of the anatomy illustrated in the X-ray image 102 that are subsequently stitched together prior to the post-processing/measurement calculation.

Looking now at FIGS. 3, in an exemplary prior art segmentation process performed on an X-ray image 202 of a pelvis, the AI model(s) 200 analyzes the image 202 to locate various landmarks/structures known to be present in an image of a pelvis, such as the femur heads, the femur shafts, the pelvic teardrops, the acetabular sourcils and the acetabular lateral edges, among others. The AI model 200 proceeds to identify and locate the landmarks within the image 202, and segments the image 202 into various representations 204 of the important and/or desired structures of the pelvis. As shown in FIG. 4, These representations 204 are subsequently combined in correspondence with their location in the image 202 to form the composite structure 206 of the pelvis from the image 202 on which the measurements are to be based. The geometric/trigonometric post-processing 208 is performed on this structure 206 in order to provide the desired angular and length measurements from the structure 206 as represented/illustrated in measurement image 210.

This measurement process results in highly accurate measurements for the anatomy represented in the X-ray image 202. However, the complexity of the computations for the image segmentation and for the post-processing requires a significant amount of memory and processing capability for the system performing the segmentation and post-processing, in addition to requiring a significant amount of time to complete.

Therefore, it is desirable to develop a system and method for automatically calculating various measurements on an anatomical structure present in an X-ray image that minimizes the computational complexity and time limitations of the prior art.

SUMMARY OF THE DISCLOSURE

According to one aspect of an exemplary embodiment of the disclosure, an artificial intelligence (AI) measurement system for an X-ray image is employed either as a component of the X-ray imaging system or separately from the X-ray imaging system to automatically scan post-exposure X-ray images to detect and locate various landmarks of the anatomy presented within the X-ray image. A set of key image features approximating the locations of the landmarks having known distance relationships to one another is overlaid onto the X-ray image. The positions of the key image features are then adjusted to correspond to the landmarks within the X-ray image. These adjustments are made relative to the prior known distance relationships between the key features, which enables the measurement system to readily calculate desired angular and length measurements between landmarks as a result.

According to another aspect of an exemplary embodiment of the disclosure, the AI measurement system can utilize key points, key lines or key areas alone or in combination with one another as the key features to calculate various angular and length measurements for an anatomy illustrated in an X-ray image.

According to another aspect of an exemplary embodiment of the disclosure, an X-ray system includes an X-ray source, an X-ray detector positionable in alignment with the X-ray ray source, and a processing unit operably connected to the X-ray source and the X-ray detector to produce X-ray images from data transmitted from the X-ray detector, wherein the processing unit includes an X-ray measurement system configured to provide an overlay of one or more key features corresponding to one or more landmarks of an anatomy within the X-ray images, and to calculate a measurement of the anatomy based on the positions of the key features within the overlay.

According to another aspect of an exemplary embodiment of the disclosure, a method of determining measurements between landmarks of an anatomy within an X-ray image includes the steps of providing an X-ray system having an X-ray source, an X-ray detector positionable in alignment with the X-ray ray source, and a processing unit operably connected to the X-ray source and the X-ray detector to produce X-ray images from data transmitted from the X-ray detector, wherein the processing unit includes an X-ray measurement system configured to provide an overlay of one or more key features corresponding to one or more landmarks of an anatomy within the X-ray images, and to calculate measurements of the anatomy based on the positions of the one or more key features in the overlay, applying the overlay to the X-ray image and calculating a measurement of the anatomy in the X-ray image based on the position of the one or more key features in the overlay applied X-ray image.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Figure 1:
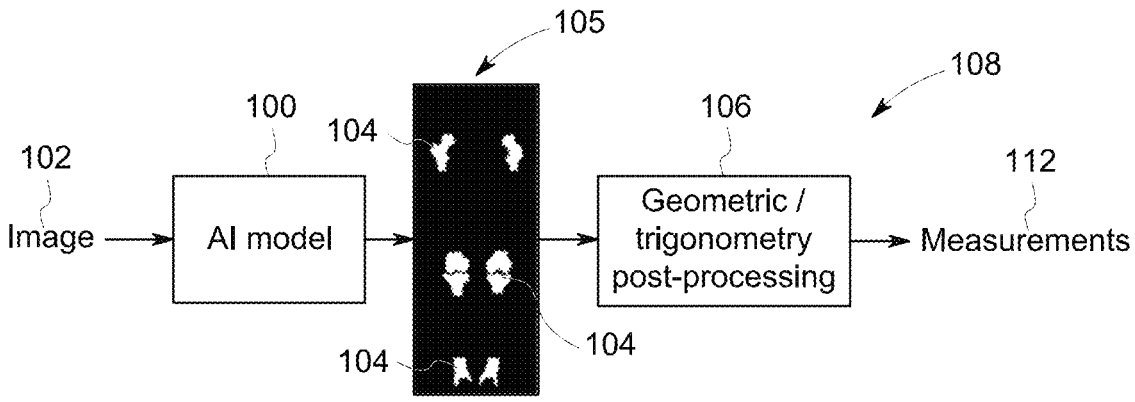
FIG. 1 is a schematic view of a first prior art measurement system for an X-ray image.
Figure 2:
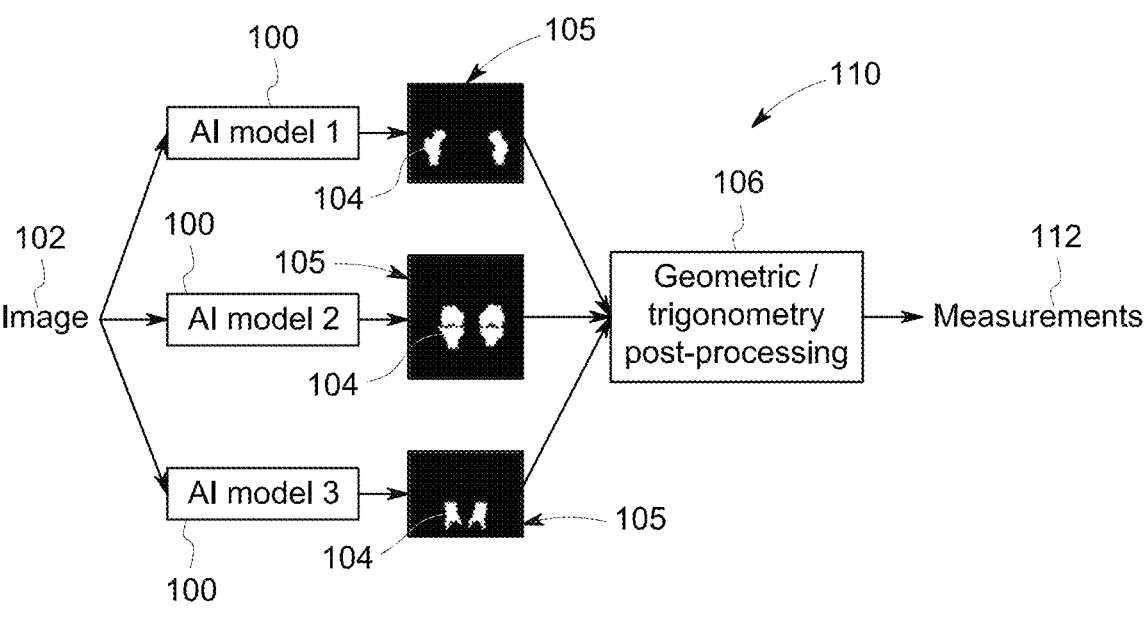
FIG. 2 is a schematic view of a second prior art measurement system for an X-ray image.
Figure 3:
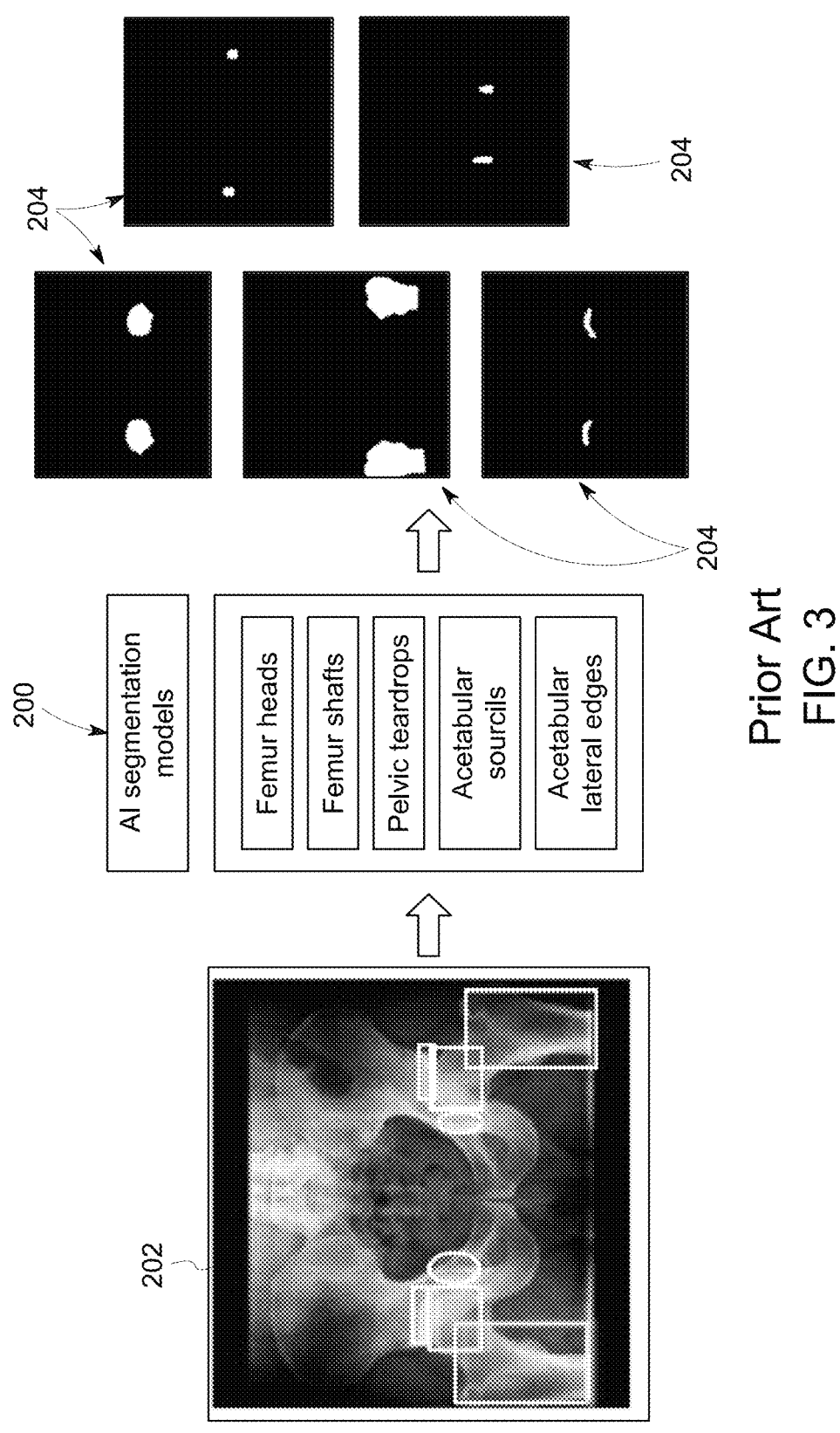
FIG. 3 is a schematic view of an image segmentation process for a prior art measurement system.
Figure 4:
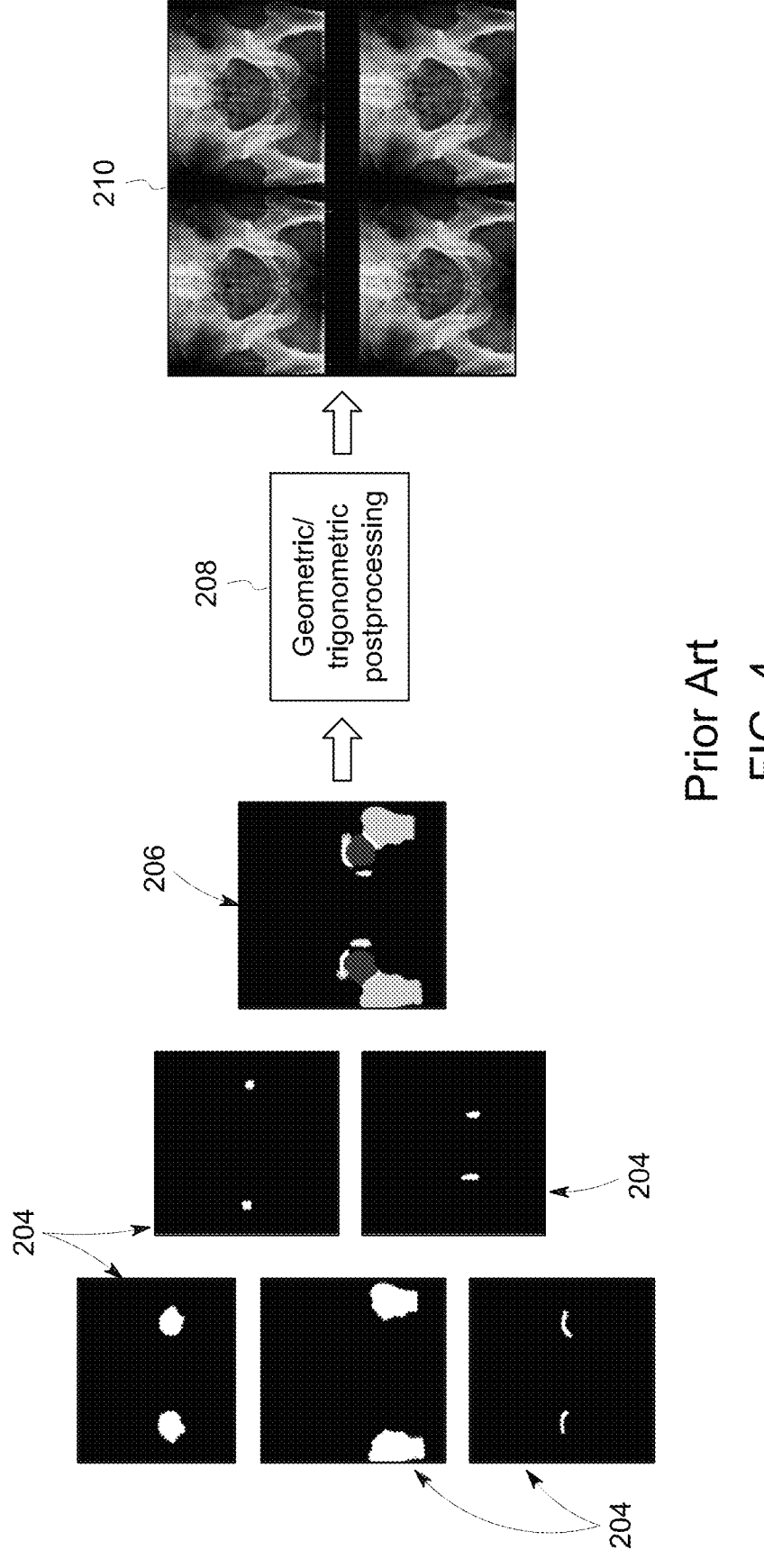
FIG. 4 is a schematic view of a measurement process for a prior art measurement system.
Figure 5:
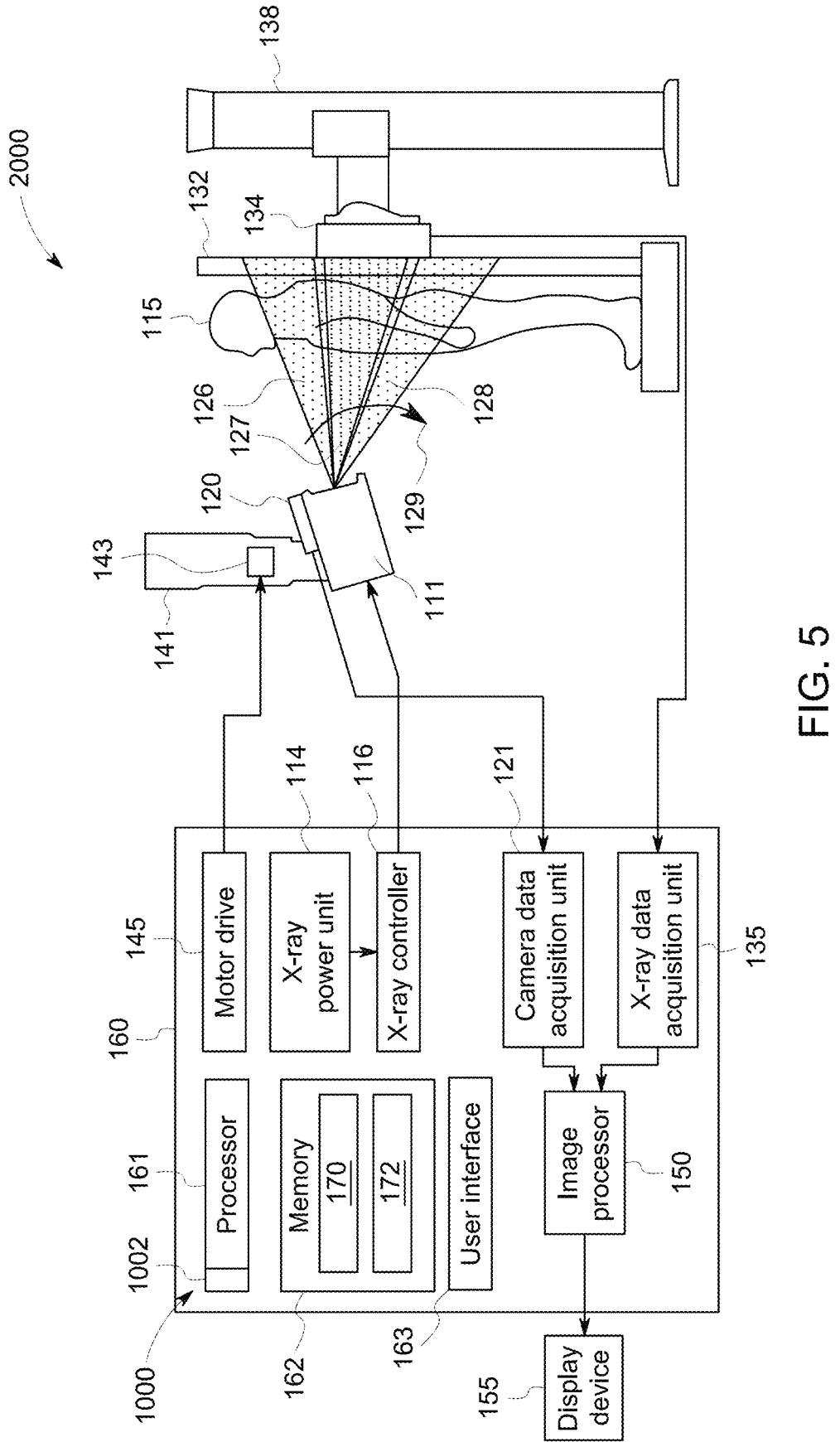
FIG. 5 is a schematic view of an X-ray imaging system employing the AI measurement system according to an exemplary embodiment of the disclosure.

Referring to FIG. 5, a block diagram of an x-ray imaging system 2000 in accordance with an embodiment is shown. The x-ray imaging system 2000 includes an x-ray source 111 which radiates x-rays, a stand 132 upon which the subject 105 stands during an examination, and an x-ray detector 134 for detecting x-rays radiated by the x-ray source 111 and attenuated by the subject 115. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 160 comprises a processor 161, a memory 162, a user interface 163, a motor drive 145 for controlling one or more motors 143, an x-ray power unit 114, an x-ray controller 116, a camera data acquisition unit 121, an x-ray data acquisition unit 135, and an image processor 150. X-ray image data transmitted from the x-ray detector 134 is received by the x-ray data acquisition unit 135. The collected x-ray image data are image-processed by the image processor 150. A display device 155 communicatively coupled to the operating console 160 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 105. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 145 of the operation console 160 may be communicatively coupled to the one or more motors 143 and configured to control the one or more motors 143. The one or more motors 143 may further be configured to adjust an angular position of the x-ray source 111 to change a field-of-view of the x-ray source 111, as described further herein.

The x-ray power unit 114 and the x-ray controller 116 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

The x-ray source 111 and the camera 120 may pivot or rotate relative to the support post 141 in an angular direction 129 to image different portions of the subject 105.

Memory 162 is a suitable electronic storage medium and/or computer-readable medium that stores x-ray images 170 and executable instructions 172 that when executed cause one or more of the processor 161 and the image processor 150 to perform one or more actions. Example methods that may be stored as the executable instructions 172 are described further herein with regard to the X-ray measurement system 1000 and AI application 1002 of FIG. 5.

The processor 161 additionally includes an automatic X-ray measurement system 1000, optionally stored in memory 162 as a part of the executable instructions 172 employed by the processor 161 to perform the functions of the measurement system 1000. While the measurement system 1000 is illustrated and described as being employed in conjunction with an X-ray system 2000, the measurement system 1000 is also contemplated as being used with other types of imaging systems, including, but not limited to, computed tomography (CT) systems, magnetic resonance (MRI) imaging systems, and ultrasound (US) systems, among other compatible imaging systems. The X-ray measurement system 1000 is formed by an artificial intelligence (AI) application 1002 that can scan and detect various types of information associated with a post-exposure X-ray image 1004 (FIGS. 6-9). The AI application 1002, which can be a deep learning neural network, for example, is an image-based object detection application that is configured for the detection various attributes of the post-exposure X-ray image 1004, such as information regarding various landmarks located in the anatomy presented within the X-ray image 1004.

Figure 6:
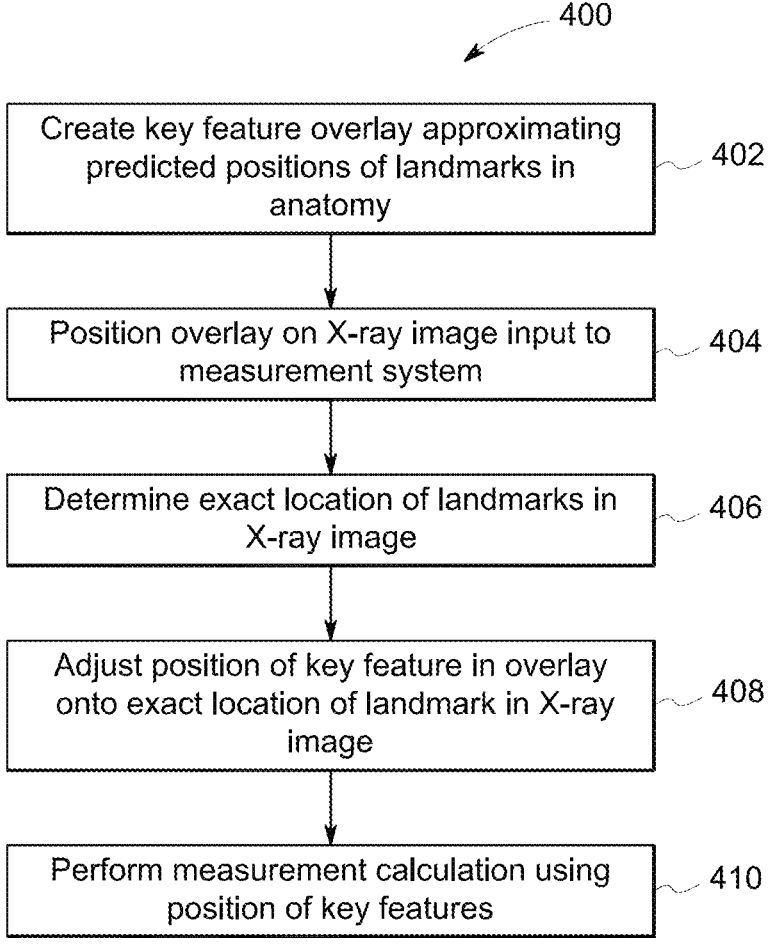
FIG. 6 is a flowchart of a method of operation of the AI measurement system according to an exemplary embodiment of the disclosure.

Referring now to FIG. 6, in an exemplary embodiment of a method 400 of operation of the X-ray measurement system 1000, initially in block 402 the AI application 1002 creates an overlay 300 (FIGS. 7A,8A) of a number of key features 302 that correspond to an estimated or approximated location of each of a corresponding number of landmarks 304 found within a selected anatomy 306 that is presented in the X-ray image 1004. The estimation of the locations of the key features 302 can be done in any suitable manner, such as a through the use of a training set of X-ray images to enable the system 1000/AI application 1002 to determine the locations of each landmark 304 in the training images and determine an average position of the landmarks 304 in the set of training images to be used for the location of the key feature(s) 302 in the overlay 300 for the anatomy 306 or for one or more different anatomies 306 present within the X-ray image 1004. In the overlay 300, the distances, angles and other measurements between each of the key features 302 is known, such that any desired measurement can be readily and directly determined from the known relationships of the positions of the key features 302 relative to one another.

In block 404, an X-ray image 1004 is supplied or input to the system 1000 and the system 1000 positions the overlay 300 onto the anatomy 306 within the X-ray image 1004, such as on the display 46, to provide a visual indication of the overlay 300 with respect to the X-ray image 1004. In block 406, the system 1000 analyzes the X-ray image 1004 utilizing any suitable image review process or method employed by the AI application 1002 in order to determine the exact locations of the landmarks 304 associated with each of the key features 302 forming the overlay 300.

After determining the exact location of each landmark 304 within the X-ray image 1004, in block 408 the AI application 1002 proceeds to adjust or edit the position of each associated key feature 302 for the landmarks 304, if necessary, such that position of the key feature 302 in the overlay 300 corresponds exactly to the location of the associated landmark 304 in the X-ray image 1004. The adjustment of the key features 302 can alternatively or in association with the AI application 1002, be conducted by the user, such as by moving the position of one or more of the key features 302 in the overly 300 on the X-ray image 1004 via the user interface 44.

With this adjustment and the corresponding known amount of the adjustment to the known distance, angle, etc. or other measurement parameter(s) between each of the key features 302 in the overlay 300, in block 410 can determine and provide a direct calculation of the desired measurements between any combination of the key features 302 and associated landmarks 304 within the X-ray image 1004. The complexity of the geometric/trigonometric calculations required in prior art measurement systems is replaced in the system 1000 by a relatively simple adjustment to the existing and known measurement parameters between the various key features 302 in the overlay 300 based on the alterations of the relative positions of the key features 302 in the overlay 300 corresponding the locations of the landmarks 304 in the X-ray image 1004. In this manner, the measurement system 1000 and AI application 1002 enable a fast and direct determination of various desired measurements between landmarks in an X-ray image 1004.

Further, in alternative embodiments for the method 400, the steps in block 404-408 can be reversed or altered in order, such that, for example, the AI application 1002 can determine the exact position of the landmarks 304 prior to without positioning the overlay 300 on the anatomy 306 in the X-ray image 1004, and/or the adjustment of the positions of the key features 302 in the overlay 300 can be performed prior to or without positioning the overlay 300 on the X-ray image 1004. Additionally, the step in block 204 of positioning the overlay 300 on the X-ray image 1004 can be moved to after the adjustment of the positions of the key features 302, in order to provide a visual representation of the overlay 300 on the anatomy 306 of the X-ray image only after all adjustments have been performed. Alternatively, the entire process of the method 400 can be maintained as an internal process within the system 1000, with no visual representation of the overlay 300 being presented, e.g., on the display 46.

With regard to the key feature(s) 302, the form of the features 302 can be selected by the user and/or by the AI application 102 as desired, such as depending upon the anatomy 306 to be presented within the X-ray image 1004, with different anatomies 306 having different key feature(s) 302. In an exemplary embodiment, the one or more key feature(s) 302 can take the form of one or more key points 312, one or more key lines 314 and/or one or more key areas 316, and combinations thereof. The various types of key features 302 can be illustrated on the display 46 in various manners, such as by changing types (e.g., points, crosses, etc.), color, size, flashing or other attributes of a key feature (s) 302 currently being analyzed and/or reviewed by the AI application 102.

Figure 7A:
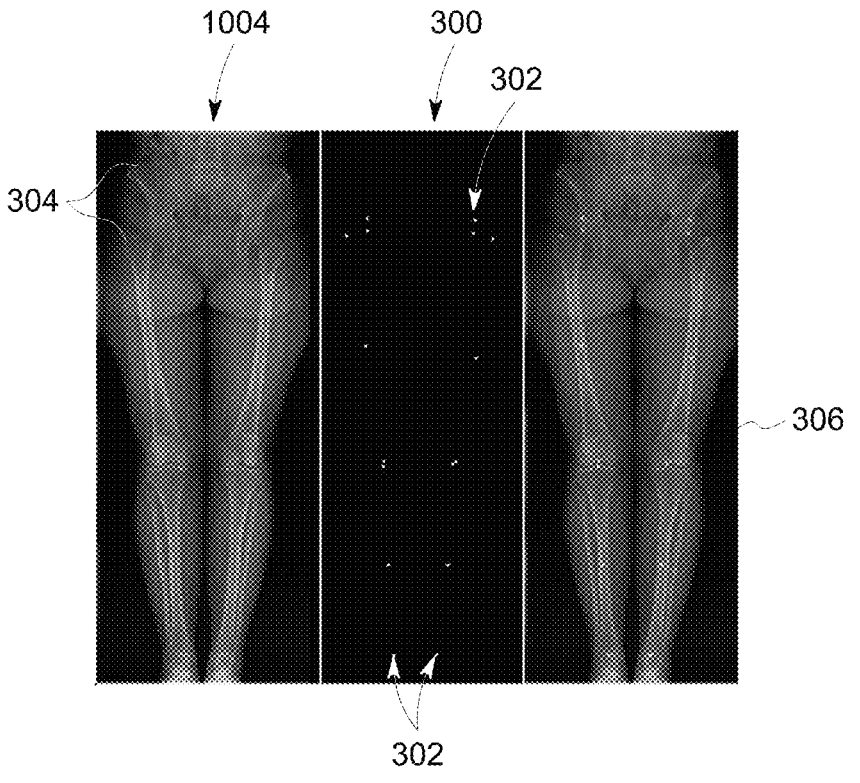
FIGS. 7A-7B are schematic views of the output of the AI measurement system according to an exemplary embodiment of the disclosure compared with a prior art segmentation measurement result.
Figure 7B:
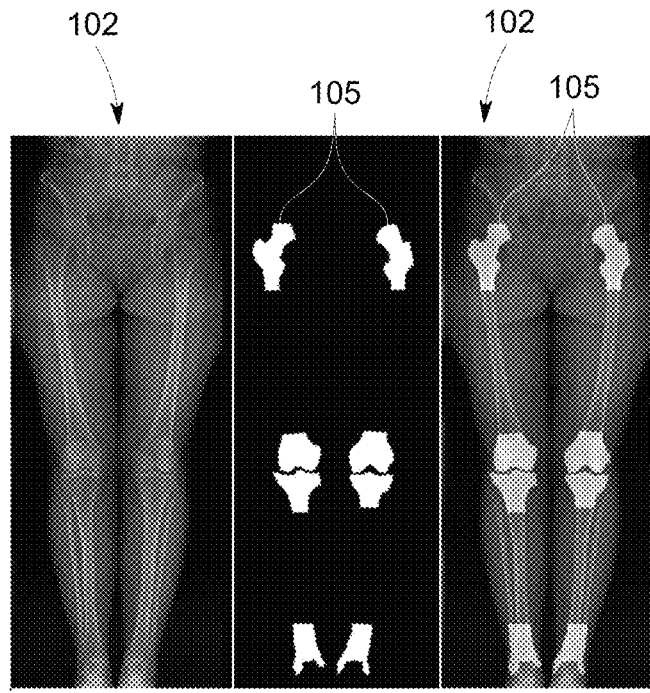

As a first example of the method 400, in FIG. 7A an anatomy 306 of an X-ray image 1004 including anatomical landmarks 304 is shown positioned next to an overlay 300 containing a number of key features 302 in the form of key points 312. The overlay 300 is also shown disposed over the anatomy 306 in the X-ray image 1004, with the positions of the key points 312 adjusted from the positions in the stand-alone overlay 300 to be disposed directly over the landmarks 304 detected in the X-ray image 1004 associated with each of the key points 312. This X-ray image 1004 is juxtaposed in FIG. 7B with a similar X-ray image 202 that has undergone a prior art segmentation to identify landmarks 204 in the image 202 and form the segmented structure 206 (also overlaid onto the image 202) on which the complex post-processing computations must be performed to provide the required measurements from the structure 206.

Figure 8A:
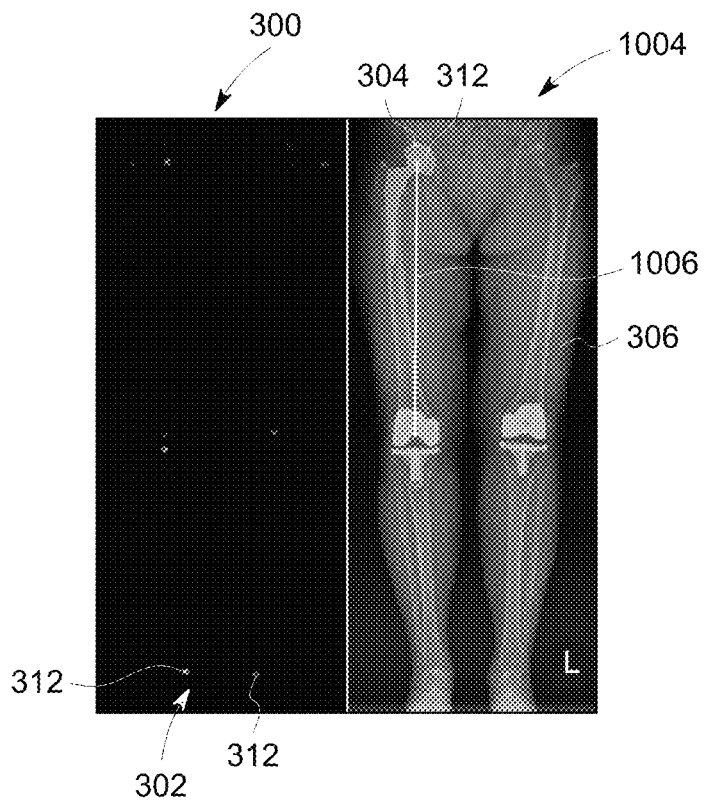
FIGS. 8A-8B are schematic views of the output of the AI measurement system according to another exemplary embodiment of the disclosure compared with a prior art segmentation result.
Figure 8B:
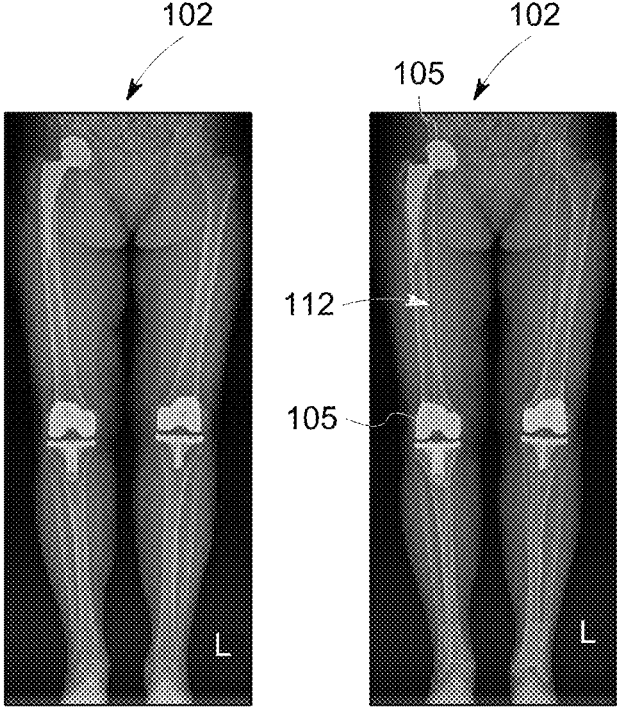

A second example of the process of the method 400 is illustrated in FIGS. 8A-8B where the overlay 300 in FIG. 8A includes a smaller number key features 302 in the form of key points 312 within the overlay 300, which are positioned over the landmarks 304 in the X-ray image 1004. The overlay 300 on the image 1004 is again compared with FIG. 8B showing the segmented structure 206 produced in the prior art method. Further, FIGS. 8A and 8B each illustrate an exemplary measurement line, with the line being a distance measurement line 212 (FIG. 8B) taken between two (2) landmarks 204 on the segmented structure 206 via the prior art method, in contrast to the distance measurement line 1006 (FIG. 8A) obtained by the system 1000 in the current method 400 corresponding to the known distance between two (2) key points 312 associated with landmarks 304 on the anatomy 306 in the X-ray image 1004.

Figure 9A:
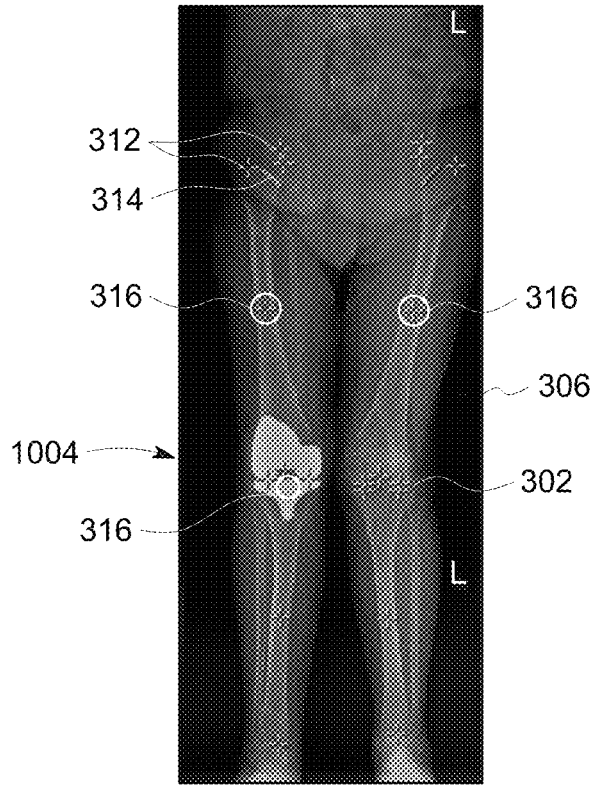
FIGS. 9A-9B are schematic views of the output of the AI measurement system using key points and key lines according to another exemplary embodiment of the disclosure.
Figure 9B:
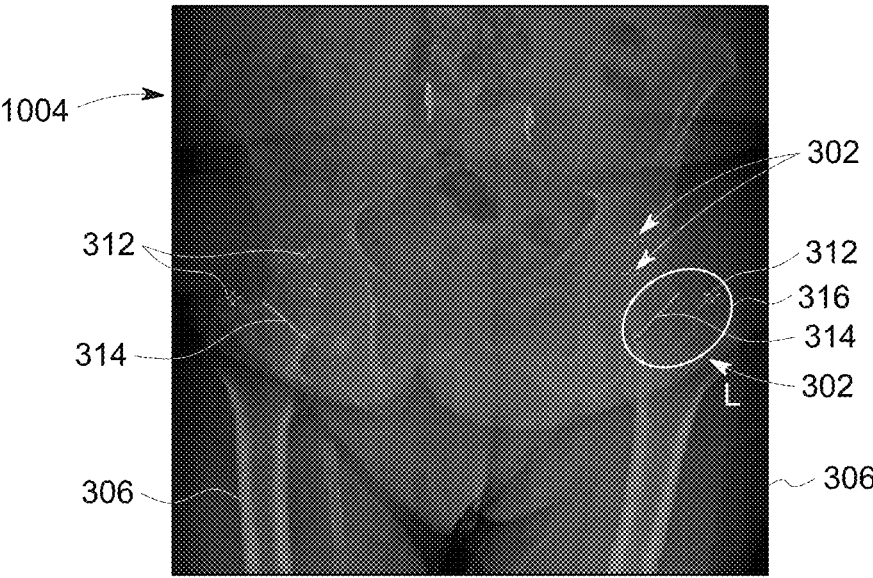

In addition, FIGS. 9A-9B illustrate an alternative embodiment of the X-ray image 1004 output by the system 1000/AI application 1002 where the overlay 300 provided on the image 1004 includes key features 302 in the form of key points 312, key lines 314 and key areas 316 corresponding to the various landmarks 304 in the X-ray image 1004. As described previously, the representations of the key points 312, key lines 314 and key areas 316 corresponding to the various landmarks 304 in the X-ray image 1004 have determined in a suitable training for the system 1000/AI application 1002 where the average locations of the key points 312, key lines 314 and key areas 316 corresponding to the various landmarks 304 in a particular anatomy 306 are determined from a dataset including a number of X-ray images 1004 of the anatomy 306 supplied to the system 1000/AI application 1002. The various key points 312, key lines 314 and key areas 316 in the anatomy 306 are subsequently adjusted automatically by the system 1000/AI application 1002 and/or manually by the user, to position the key points 312, key lines 314 and key areas 316 directly over the corresponding landmarks in the anatomy 306 to form the overlay 300. In this configuration, the system 1000/AI application 1002 can readily calculate the required measurements within the anatomy 306 presented in the X-ray image 1004 based on the prior know relationships between the various key points 312, key lines 314 and key areas 316 and the adjustments made to these relationships in the formation of the overlay 300. Further, the system 1000/AI application 1002 can be trained to Finally, it is also to be understood that the system 1000AI application 1002 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semi-conductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the system 10,1000 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method of determining measurements between landmarks of an anatomy within an X-ray image comprising the steps of:

providing an X-ray system comprising:

an X-ray source;

an X-ray detector positionable in alignment with the X-ray ray source; and a processing unit operably connected to the X-ray source and the X-ray detector to produce X-ray images from data transmitted from the X-ray detector, wherein the processing unit includes an X-ray measurement system configured to provide an overlay of one or more key features corresponding to one or more landmarks of an anatomy within the X-ray images, and to calculate measurements of the anatomy based on the positions of the one or more key features in the overlay;

applying the overlay to the X-ray image;

adjusting the position of the one or more key features within the overlay into alignment with the associated landmark in the X-ray image; and calculating a measurement of the anatomy in the X-ray image based on the position of the one or more key features in the overlay applied X-ray image, wherein the X-ray measurement system is formed of an artificial intelligence (AI) trained to provide the overlay including an average position of the one or more key features corresponding to the one or more landmarks of the anatomy.

2. The method of claim 1, wherein the AI is trained to provide the overlay including an average position of the one or more key features corresponding to the one or more landmarks of multiple anatomies.

3. The method of claim 1, wherein the AI is configured to provide the overlay with at least one of a key point, a key line and a key area corresponding to the one or more key features corresponding to the one or more landmarks of the anatomy.

4. The method of claim 1, wherein the step of applying the overlay to the X-ray image comprises presenting the overlay in conjunction with the X-ray image on a display.

5. The method of claim 4, wherein the step of presenting the overlay in conjunction with the X-ray image comprises placing the overlay over the X-ray image on the display.

6. The method of claim 1, wherein the step of adjusting the position of the one or more key features within the overlay into alignment with the associated landmark in the X-ray image is performed automatically by the X-ray measurement system.

7. The method of claim 1, wherein the step of adjusting the position of the one or more key features within the overlay into alignment with the associated landmark in the X-ray image is performed manually.

8. The method of claim 7, wherein the step of applying the overlay to the X-ray image comprises presenting the overlay in conjunction with the X-ray image on a display, and wherein the step of manually adjusting the position of the one or more key features within the overlay comprises moving the one or more key features within the overlay on the display into alignment with the one or more landmarks in the X-ray image.

9. The method of claim 1, wherein the position of the one or more key features within the overlay is known, and wherein the step of calculating the measurement of the landmarks in the anatomy based on the position of the one or more key features in the overlay comprises determining the measurement of one key feature relative to another key feature.

10. The method of claim 9, wherein the step of calculating the measurement of the landmarks in the anatomy based on the position of the one or more key features relative to the landmarks in the X-ray image comprises determining the measurement of one key feature relative to an adjusted key feature.

11. The method of claim 10, wherein the step of adjusting the position of the one or more key features within the overlay relative to the one or more landmarks in the X-ray image comprises:

moving the one or more key features to align the one or more key features with a corresponding landmark in the anatomy; and determining an adjusted position of the one or more key features within the overlay.

12. The method of claim 9, wherein the step of calculating the measurement of the landmarks in the anatomy based on the position of the one or more key features relative to the landmarks in the X-ray image comprises determining the measurement of one adjusted key feature relative to another adjusted key feature.

13. An X-ray system comprising:

an X-ray source;

an X-ray detector positionable in alignment with the X-ray ray source; and a processing unit operably connected to the X-ray source and the X-ray detector to produce X-ray images from data transmitted from the X-ray detector, wherein the processing unit includes an X-ray measurement system configured to provide an overlay of one or more key features corresponding to one or more landmarks of an anatomy within the X-ray images, to adjust the position of the one or more key features within the overlay into alignment with the associated landmark in the X-ray image and to calculate a measurement of the anatomy based on the positions of the key features within the overlay, wherein the X-ray measurement system does not employ image segmentation to provide the overlay of one or more key features corresponding to one or more landmarks of an anatomy within the X-ray images, and wherein the X-ray measurement system is formed of an artificial intelligence (AI), and wherein the AI is trained to provide the overlay including an average position of the one or more key features corresponding to the one or more landmarks of the anatomy.

14. The X-ray system of claim 13, wherein the position of the one or more key features within the overlay is known, and wherein the AI is configured to calculate the measurement of the anatomy based on the position of the one or more key features in the overlay by determining a measurement of one key feature relative to another key feature.

15. The X-ray system of claim 13, wherein the AI is configured to calculate the measurement of the anatomy based on the position of the one or more key features in the overlay by determining the measurement of one key feature relative to another key feature.

16. The X-ray system of claim 13, wherein the AI is configured to calculate the measurement of the anatomy based on the position of the one or more key features relative to the landmarks in the X-ray image by determining the measurement of one adjusted key feature relative to another adjusted key feature.

* * * * *